(12) United States Patent
Wang et al.

(10) Patent No.: US 8,528,425 B2
(45) Date of Patent: Sep. 10, 2013

(54) SAMPLING COMPONENT, SAMPLING DEVICE AND ION MOBILITY SPECTROMETER

(75) Inventors: Yaoxin Wang, Beijing (CN); Yangtian Zhang, Beijing (CN); Jin Lin, Beijing (CN); Bin Xue, Beijing (CN); Wen He, Beijing (CN); Hua Peng, Beijing (CN); Peng Jiao, Beijing (CN)

(73) Assignee: Nuctech Company Limited, Beijing (CN)

( * ) Notice: Subject to any disclaimer, the term of this patent is extended or adjusted under 35 U.S.C. 154(b) by 250 days.

(21) Appl. No.: 12/737,341

(22) PCT Filed: Dec. 1, 2010

(86) PCT No.: PCT/CN2010/001937
§ 371 (c)(1),
(2), (4) Date: Dec. 30, 2010

(87) PCT Pub. No.: WO2011/075940
PCT Pub. Date: Jun. 30, 2011

(65) Prior Publication Data
US 2011/0290041 A1    Dec. 1, 2011

(30) Foreign Application Priority Data

Dec. 24, 2009  (CN) .......................... 2009 1 0243787

(51) Int. Cl.
*G01N 1/22*       (2006.01)
(52) U.S. Cl.
USPC ...................................................... 73/863.11
(58) Field of Classification Search
USPC .................. 73/863.11, 863.12, 863.23, 28.04
See application file for complete search history.

(56) References Cited

U.S. PATENT DOCUMENTS

| 5,585,575 | A  | * | 12/1996 | Corrigan et al. ............ 73/863.71 |
| 5,859,375 | A  |   | 1/1999 | Danylewych-May et al. |
| 6,572,825 | B1 |   | 6/2003 | Linker et al. |
| 7,299,710 | B2 | * | 11/2007 | Syage ........................ 73/863.12 |

(Continued)

FOREIGN PATENT DOCUMENTS

| CA | 2744295 | 6/2010 |
| CN | 101363778 | 2/2009 |

(Continued)

OTHER PUBLICATIONS

German Office Action dated Jun. 6, 2011 in Application No. 11 2010 000 009.3.

(Continued)

*Primary Examiner* — Jewel V Thompson
(74) *Attorney, Agent, or Firm* — Staas & Halsey LLP

(57) ABSTRACT

A sampling component including a sampling body that can be electrically heated and an outer surface of which has a wiping sampling area to receive a sample; and an insulated handle that is connected to one longitudinal end of the sampling body. The sampling component contacts directly electrical contacts of an external power supply after being positioned in a analysis chamber, the power supply is turned on to vaporize the sample, and the power is turned off immediately after the sampling component removed from the chamber. The power consumption and a malfunction caused by long-term use of the sampling device under a high temperature can be avoided. A sampling device having the sampling component and an ion mobility spectrometer having the sampling device are also provided.

14 Claims, 2 Drawing Sheets

(56) References Cited

U.S. PATENT DOCUMENTS

| | | | |
|---|---|---|---|
| 7,299,711 | B1 | 11/2007 | Linker et al. |
| 7,947,959 | B2 | 5/2011 | Stratton |
| 7,997,119 | B2 * | 8/2011 | Wu .............................. 73/31.03 |
| 2001/0042413 | A1 | 11/2001 | Sakairi et al. |
| 2007/0034024 | A1 | 2/2007 | Syage |
| 2009/0289183 | A1 | 11/2009 | Chen et al. |

FOREIGN PATENT DOCUMENTS

| | | |
|---|---|---|
| CN | 101438141 | 5/2009 |
| DE | 10-2009-020839 | 12/2009 |
| DE | 10 2008 059112 | 6/2010 |
| EP | 1434050 | 6/2004 |
| JP | 2008-3016 | 1/2008 |
| JP | 2008-304340 | 12/2008 |

OTHER PUBLICATIONS

Partial English Translation of Second German Office Action in Application No. 11 2010 000 009.3.

International Search Report dated Mar. 10, 2011 in Application No. PCT/CN2010/001937.

Written Opinion of the International Search Report dated Mar. 10, 2011 in Application No. PCT/CN2010/001937.

International Preliminary Report on Patentability and the Written Opinion of the International Searching Authority issued Jun. 26, 2012 issued in International Patent Application No. PCT/CN2010/001937.

* cited by examiner

SAMPLING COMPONENT, SAMPLING DEVICE AND ION MOBILITY SPECTROMETER

This application claims the benefit under U.S.C. Section 371, of PCT International Application No. PCT/CN2010/001937, filed Dec. 1, 2010 and Japanese Application No. 2009-10243787.3 filed Dec. 24, 2009, the contents of which are incorporated herein by reference.

TECHNICAL FIELD

The present invention relates to a sampling component, a sampling device having the sampling component and an ion mobility spectrometer having the sampling device, particularly relates to an ion mobility spectrometer for detecting explosives and drugs, and a sampling component of the ion mobility spectrometer having a sample pyrolysis function and a sampling device using the sampling component.

BACKGROUND OF THE INVENTION

Traditionally, the sampling component in the ion mobility spectrometer for detecting explosives and drugs is used for wiping samples from the surface of the sampled object, or absorbing the sample from the air by means of external forces, then the sampling component carried with the sample is disposed into the analysis chamber of the sampling device of the ion mobility spectrometer, the inner of the analysis chamber is heated from the outside of the sampler, such that the sample is heated passively so as to be separated from the sampling component for detection.

The traditional sampling components are usually objects such as paper sheets, flake articles, which are placed in the analysis chamber of the sampler and heated by heating the analysis chamber from the outside of the sampler so as to thermally parse the sample.

Since the sampling component is heated by heating the inner of the analysis chamber from the outside of the sampler so as to vaporize the sample, the heating time is long, thereby, the parsing and detecting efficiency is low. In addition, in order to effectively and quickly parse the sample and avoid preheating the inner of the analysis chamber every time the sample is parsed, the analysis chamber of the sampler is required to be in the high temperature working environment all along, i.e., the analysis chamber needs to be heated from the outside all along, which may result in increase of power consumption, even system malfunction of the sampler.

SUMMARY OF THE INVENTION

The present invention aims to solve one of the technical problems existing in the prior art.

To this end, the object of the first aspect of the present invention lies in proposing a sampling component, the sampling component itself can be electrically heated so as to have a pyrolysis function, besides, the parsing and detecting efficiency of the sample is high when using the sampling component.

The sampling component according to the embodiment of the first aspect of the present invention comprises a sampling body that can be electrically heated and the outer surface of the sampling body has a wiping sampling area; and an insulated handle that is connected with one longitudinal end of the sampling body.

As for the sampling component according to the embodiments of the present invention, the sampling body can be electrically heated, hence, when the sampling component is placed into the analysis chamber of the sampler, the sampling body can be electrically heated, so that the sample on the sampling body is heated and parsed without heating the whole analysis chamber of the sampler, thus, the parsing efficiency is improved and the power consumption is reduced. And the power is off immediately after the sampling component is taken away. Thus, the power supply of the sampler can work discontinuously so that the power consumption of the system is reduced and the length of life can be increased.

In addition, the sampling component is provided with an insulated handle for the convenience of holding the sampling component, which is convenient and safe.

Moreover, the sampling component according to the embodiments of the present invention further comprises the following additional technical features:

The sampling body is made of a conductive material.

The sampling body is in a laminated structure or a tubular structure.

The wiping sampling area is provided with a plurality of throughholes or protrusions.

The surface area of the wiping sampling area can be increased by arranging throughholes and protrusions in the wiping sampling area, which is convenient for the sampling component to carry the samples. In addition, the two surfaces of the sampling body can be connected by arranging throughholes, and when being placed into the analysis chamber of the sampler, it is easy for the sample on the lower surface to move up through the throughholes, so as to facilitate sample parsing.

First and a second contacts are arranged respectively at two sides of the wiping sampling area along a longitudinal direction of the sampling body.

The first and second contacts arranged at the two sides of the wiping sampling area correspond to the contacts within the analysis chamber of the sampler. When the sampling component is placed into the analysis chamber, it is convenient for electrically heating the sampling body through the corresponding contacts.

The object of the second aspect of the present invention lies in proposing a sampling device having the sampling component according to the first aspect of the present invention, the sampling device can electrically heat the sampling component itself, so as to improve the pyrolysis efficiency of the sample, and can work discontinuously so as to reduce the power consumption and increase the length of life.

The sampling device according to the embodiment of the second aspect of the present invention comprises: a sampler comprising a housing, the inner of which defines a analysis chamber and one end of which is provided with an opening; a power supply; and a third and a fourth contacts, the first ends of the third and fourth contacts being respectively extended into the analysis chamber and the second ends thereof being respectively connected with the anode and cathode of the power supply; and a sampling component that is adapted to be placed into the analysis chamber from the opening of the housing and supported by the first ends of the third and fourth contacts so as to be electrically heated.

The sampling device according to the present invention only electrically heats the sampling component when the sampling component is placed into the analysis chamber, the power is off immediately after the sampling component is taken out, it is not necessary to electrically heat the analysis chamber all the time, so that the power can be on and off at any moment, the power consumption is reduced, the system malfunction caused by a long-term work of the sampler under a high temperature is avoided, and the working environment of the system is improved.

The object of the third aspect of the present invention lies in proposing an ion mobility spectrometer having the sampling device according to the second aspect of the present invention. The ion mobility spectrometer enters into the detector for detection after the sample in the sampling device is heated and vaporized.

The ion mobility spectrometer according to the embodiment of the third aspect of the present invention comprises a detector and a sampling device, wherein the sampling device is the sampling device according to the second aspect of the present invention, wherein the detector is connected with the analysis chamber of the housing of the sampling device via a channel.

The detector is connected with the analysis chamber at the other end to which the opening of the housing corresponds.

The additional aspects and advantages of the present invention will be presented in the following description, some will become obvious through the following description, or will be understood from the practice of the present invention.

DESCRIPTION OF THE DRAWINGS

The above mentioned and/or additional aspects and advantages of the present invention will become obvious and easy to understand from the description of the embodiments with reference to the following drawings, wherein:

FIG. 2 is a schematic diagram of the sampling device according to the embodiments of the present invention, wherein the power supply is not turned on;

FIG. 3 is a schematic diagram of the sampling device as shown in FIG. 2 when the power supply is turned on.

DESCRIPTION OF THE EMBODIMENTS

Figure 1:
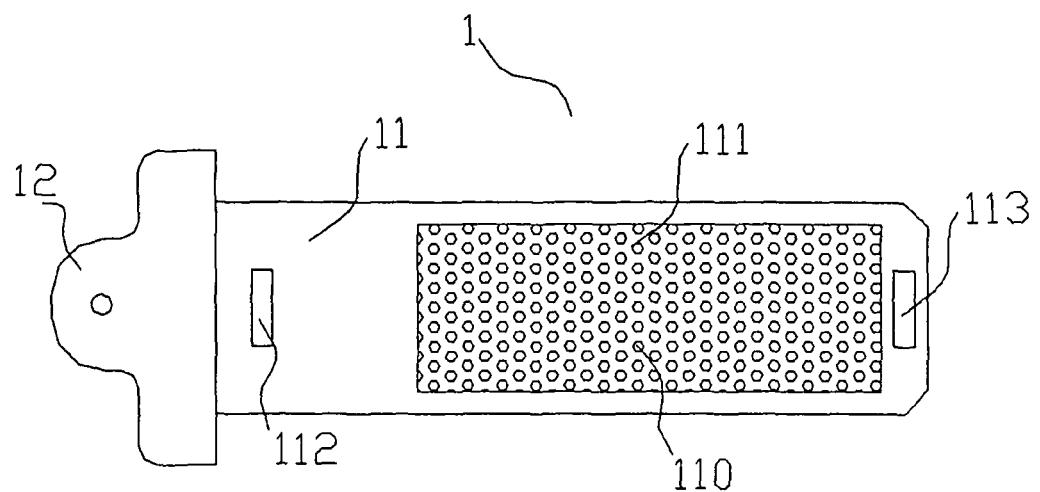
FIG. 1 is a front view of the sampling component according to the embodiments of the present invention.

The embodiments of the present invention will be described in detail as follows. The examples of the embodiments are shown in the drawings, wherein the all along same or similar marks represent the same or similar components or components having the same or similar functions. The following embodiments described with reference to the drawings are exemplary and are only used to explain the present invention, while cannot be construed as limitations to the present invention.

In the description of the present invention, the term "longitudinal direction" refers to the direction based on the orientation and positional relation as shown in the drawings, which is only for the convenience of describing the present invention instead of requiring the present invention to be constructed and operated in a particular orientation, hence, it cannot be construed as limitation to the present invention.

The sampling component according to the embodiments of the present invention will be described in detail as follows with reference to the drawings.

As shown in FIG. 1, a sampling component 1 according to an embodiment of the present invention comprises a sampling body 11 and an insulated handle 12. The sampling body 11 can be electrically heated, and the outer surface of the sampling body 11 has a wiping sampling area 111 for wiping the sample or absorbing the sample by means of external forces, so as to carry the sample on the sampling component 1. The insulated handle 12 is used to hold the sampling component 1, provides convenience and safety for operating and using the sampling component 1, and is connected to one longitudinal end of the sampling body 11.

As shown in FIG. 1, according to one example of the present invention, the sampling body 11 can be made of thermal electric conductive material (such as copper), and be in a laminated structure. Of course, the present invention is not limited to this, the sampling body 11 can be made of any appropriate material, as long as it can be electrically heated.

The sampling body 11 can be electrically heated. The sampling body 11 can be quickly heated to a high temperature by setting a relatively high heating power for the sampling body 11. It can be quickly heated to above 200° within 2-4 seconds, thus, the pyrolysis efficiency and detecting efficiency are improved.

In addition, during use of the sampling component 1, the operator can control the heating curve of the sampling body 11 to pass through the optimal pyrolysis temperature points of all the samples.

Optionally, the sampling body 11 is not limited to the laminated structure, for example, it can be a tubular structure or structures of other shapes.

The wiping sampling area 111 occupies a relatively large area on the outer surface of the sampling body 11 so as to be convenient for wiping and carrying the samples. According to one example of the present invention, as shown in FIG. 1, the wiping sampling area 111 is provided with a plurality of throughholes 110 so that the wiping sampling area 111 forms a mesh pore structure. By arranging throughholes 110, on the one hand, the area of the wiping sampling area 111 is increased and, on the other hand, when the sampling component 1 is placed into the analysis chamber 22 (see FIG. 2), the samples on the lower surface of the sampling body 11 can move up through the throughholes 110, so as to be convenient for the detector T to detect the samples.

Optionally, the wiping sampling area 111 can be provided with a plurality of protrusions so as to increase the surface area of the wiping sampling area 111.

In one example of the present invention, a first contact 112 and a second contact 113 are respectively arranged at two sides of the wiping sampling area 111 along a longitudinal direction (right and left direction in FIG. 1) of the sampling body 11. The first contact 112 and the second contact 113 are used to contact a first end 24a of a third contact 24 and a first end 25a of a fourth contact 25 in the analysis chamber 22 so as to electrically heat the sampling body 11.

The sampling device having said sampling component 1 according to the embodiments of the present invention will be described as follows with reference to FIG. 2 and FIG. 3.

Figure 2:
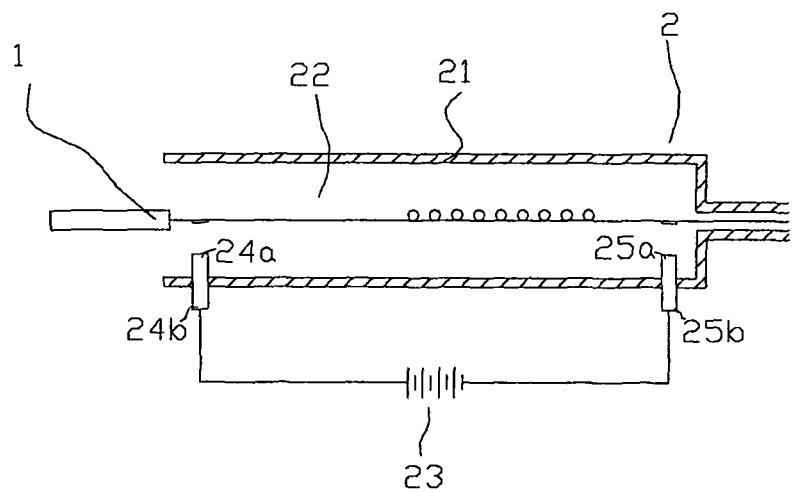
Figure 3:
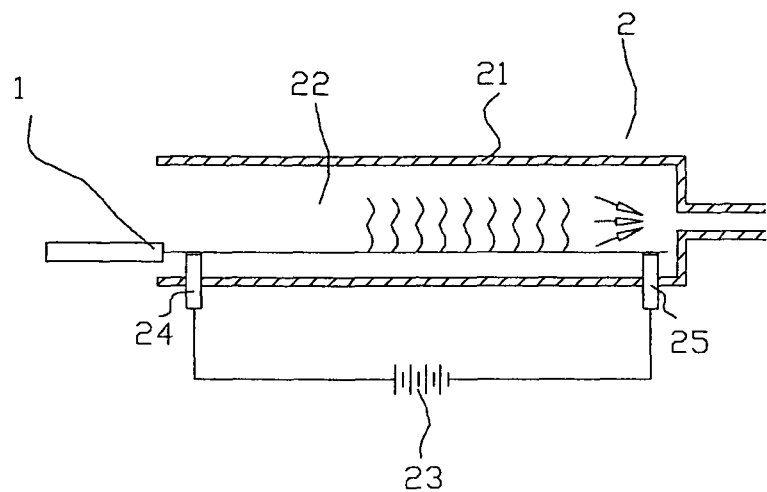

As shown in FIG. 2, the sampling device according to the embodiments of the present invention comprises a sampling component 1 and a sampler 2. The sampler comprises a housing 21, a pyrolysis power supply 23, the third contact 24 and the fourth contact 25. The inside of the housing 21 defines a analysis chamber 22, one end of the housing 21 is provided with an opening for accommodating the sampling component, the other end is adapted to be connected with the detector T (see FIG. 4) via a channel 26. The channel 26 may be either a portion of the housing 21, or a separate component.

The third contact 24 and the fourth contact 25 respectively correspond to the first contact 112 and the second contact 113. The first end 24a of the third contact 24 and the first end 25a of the fourth contact 25 are respectively extended into the analysis chamber 22. When the sampling component 1 is placed into the analysis chamber 22 from the opening of the housing 21, the sampling component 1 is supported by the first end 24a of the third contact 24 and the first end 25a of the fourth contact 25, and the first contact 112 and the second contact 113 on the sampling body 11 respectively contact the first end 24a of the third contact 24 and the first end 25a of the fourth contact 25.

A second end 24b of the third contact 24 and a second end 25b of the fourth contact 25 are located outside of the analysis chamber 22 and are respectively connected to the anode and cathode of the pyrolysis power supply 23. Thus, when the sampling component 1 is placed into the analysis chamber 22 of the sampler 2, the sampling component 1 and the pyrolysis power supply 23 form a loop so that the sampling component 1 is electrically heated and the sample is heated and parsed. After the sampling component 1 is taken away, the loop is turned off, thus the pyrolysis power supply 23 of the sampler 2 can work discontinuously, so that the power consumption is reduced, and it is not necessary for the inside of the analysis chamber 22 to remain at a high temperature all the time, so that the length of life of the sampling device is increased, besides, it does not need to be preheated, so that the efficiency is improved.

The pyrolysis operation of the sampling device according to the embodiments of the present invention will be described as follows with reference to FIG. 2 and FIG. 3.

As shown in FIG. 2, after the sampling component 1 collects samples such as explosives and drugs by wiping samples from the surface of the sampled object or by absorbing the samples from the air by means of external forces, the sampling component 1 is placed into the analysis chamber 22 of the sampler 2. The first contact 112 and the second contact 113 respectively contact the first end 24a of the third contact 24 and the first end 25a of the fourth contact 25, such that the sampling component 1 and the pyrolysis power supply 23 form an electrical loop, which begins to heat the sample so that the sample is heated and vaporized, as shown in FIG. 3, of course, a switch (not shown) may also be arranged between the first end 24a of the third contact 24 and the first end 25a of the fourth contact 25, when the sampling component 1 is placed into the analysis chamber 22, the switch is turned on so as to heat and vaporize the sample. When the sampling component 1 is taken out or the sampling component 1 is not taken out but the switch is turned off, the electrical loop is off, the pyrolysis power supply 23 of the sampler 2 stops working.

Figure 4:
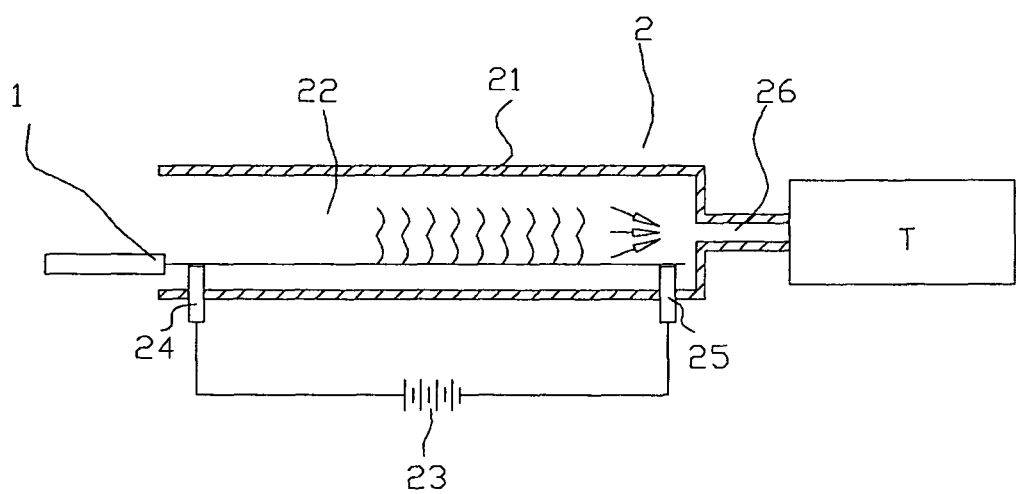
FIG. 4 is a structural schematic diagram of the ion mobility spectrometer according to the embodiments of the present invention.

The ion mobility spectrometer having said sampling device according to the embodiments of the present invention will be described as follows with reference to FIG. 4.

The ion mobility spectrometer according to the embodiments of the present invention comprises the detector T and said sampling device, wherein the detector T is connected with the analysis chamber 22 within the housing 21 of the sampling device via the channel 26.

The operation of the ion mobility spectrometer is as follows: when the sample in the sampling device is heated and vaporized, the vaporized sample enters into the detector T through the channel 26 between the sampler 2 and the detector T, a receiving portion in the detector T can receive different vaporized samples and form a mass spectrogram, so as to determine the detected object.

Although the embodiments of the present invention have been shown and described, one skilled in the art can understand that many variations, modifications, replacements and transformations can be made to these embodiments in the case of not deviating from the principle and tenet of the present invention. The scope of the present invention is defined by the claims and the equivalents thereof.

What is claimed is:

1. A sampling device, comprising:
   a sampler, including—
       a housing, an inside of which defines an analysis chamber and one end of which is provided with an opening;
       a power supply; and
       two contacts, first ends of which are respectively extended into the analysis chamber and second ends of which are respectively connected with an anode and a cathode of the power supply; and
   a sampling component capable of being electrically heated and an outer surface of which has a wiping sampling area thereon, and an insulated handle connected to one longitudinal end of the sampling component,
   wherein the sampling component is adapted to be placed into the analysis chamber from the opening of the housing and supported by the first ends of the contacts so as to be electrically heated.

2. An ion mobility spectrometer, comprising: a detector and a sampling device according to claim 1, wherein the detector is connected with the analysis chamber via a channel.

3. The ion mobility spectrometer according to claim 2, wherein the detector is connected with the analysis chamber via the channel at an opposite end of the housing from the opening.

4. A sampling device, comprising:
   a sampler, including—
       a housing, the inner of which defines a analysis chamber and one end of which is provided with an opening,
       a power supply, and
       a third and a fourth contacts, the first ends of the third and fourth contacts being respectively extended into the analysis chamber and the second ends thereof being respectively connected with the anode and cathode of the power supply; and
   a sampling component including—
   a sampling body capable of being electrically heated and the outer surface of the sampling body has a wiping sampling area,
   an insulated handle connected with one longitudinal end of the sampling body,
   and first and second contacts on the sampling body,
   wherein the sampling component is adapted to be placed into the analysis chamber from the opening of the housing and the first and second contacts are supported by the first ends of the third and fourth contacts so as to electrically heat the sampling component.

5. An ion mobility spectrometer, comprising: a detector and a sampling device, wherein the sampling device is a sampling device according to claim 4, wherein the detector is connected with the analysis chamber of the housing of the sampling device via a channel.

6. An ion mobility spectrometer according to claim 5, wherein the detector is connected with the analysis chamber at the other end of the housing.

7. The sampling device according to claim 1, wherein the sampling component includes a sampling body made of electrically conductive material.

8. The sampling device according to claim 1, wherein the sampling component includes a sampling body which is a sheet structure.

9. The sampling device according to claim 1, wherein the sampling component includes a sampling body which is a tubular structure.

10. The sampling device according to claim 1, wherein the wiping sampling area is provided with a plurality of through-holes.

11. The sampling device according to claim 1, wherein the wiping sampling area is provided with a plurality of protrusions.

12. The sampling device according to claim 1, wherein first and a second contacts are arranged respectively at two opposite longitudinal ends of the sampling component.

13. The sampling device according to claim 1, wherein the sampling component can be heated to a temperature above 200° within 2-4 seconds.

14. The sampling device according to claim 1, wherein during use of the sampling component, a user can control a heating curve of the sampling component to pass through optimal pyrolysis temperature points of samples to be detected.

* * * * *

UNITED STATES PATENT AND TRADEMARK OFFICE
CERTIFICATE OF CORRECTION

PATENT NO. : 8,528,425 B2  
APPLICATION NO. : 12/737341  
DATED : September 10, 2013  
INVENTOR(S) : Yaoxin Wang et al.

It is certified that error appears in the above-identified patent and that said Letters Patent is hereby corrected as shown below:

Title Page, In Col. 2 (Abstract), Line 10, After "consumption" insert -- is reduced --.

In the Specification

Col. 1, Line 7, Delete "Japanese" and insert -- Chinese --, therefor.

Signed and Sealed this  
Twenty-fourth Day of December, 2013

Margaret A. Focarino  
*Commissioner for Patents of the United States Patent and Trademark Office*